United States Patent [19]

Bitakaramire

[11] 4,314,992
[45] Feb. 9, 1982

[54] PROCESS FOR PRODUCING FASCIOLIASIS VACCINE

[75] Inventor: Peter K. Bitakaramire, Nairobi, Kenya

[21] Appl. No.: 92,259

[22] Filed: Nov. 6, 1979

[30] Foreign Application Priority Data

Nov. 8, 1978 [GB] United Kingdom ............... 43695/78
Feb. 5, 1979 [GB] United Kingdom ............... 03989/79

[51] Int. Cl.$^3$ ...................... A61K 41/00; A61K 35/56
[52] U.S. Cl. ...................................................... 424/88
[58] Field of Search .......................................... 424/88

[56] References Cited

FOREIGN PATENT DOCUMENTS 819830 9/1959 United Kingdom .................. 424/88
902760 8/1962 United Kingdom .................. 424/88

OTHER PUBLICATIONS

Bitakaramire, P. K., (1973) Isotopes and Radiation in Parasitology III: 23–32, Preliminary Studies on the Immunization of Cattle Against Fascioliasis Using Gamma-irradiated Metacercariae of Fasciola Gigantica.

Bitakaramire, P. K., (1968) Parasitology 58: 653–656, Lymnaea Natalensis Laboratory Culture and Production of Fasciola Gigantica Metacercariae.

Boray, J. C., Proc. 3rd. Int. Conf. World Assoc. for Adv. Vet. Parasitology pp. 84–95 (1967), The Effect of Host Reaction to Experimental Fasciola Hepatica Infections in Sheep and Cattle.

Hughes, D. L., Nature 193 (4820): 1093–1094, Mar. 17, 1962, Reduction of the Pathogenicity of Fasciola Hepatica in Mice by X-irradiation.

Nansen, P., Res. Vot. Sci. 19: 278–283 (1975) Resistance in Cattle to Fasciola Hepatica Induced by X-ray Attenuated Larvae: Results from a Controlled Field Trial.

Mulligan, W., Preparation of Radiation Attenuated Vaccines Against Horminthic Infections, pp. 1–11 (1973) IAEA (1975) Nuclear Techniques in Helminthology Research Proc. Panel.

Mulligan, W., Nuclear Techniques in the Control of Parasitic Infections, pp. 413–419, IAEA (1976) Int. Symp. Nuclear Techniques in Animal Production and Health, Vienna 1976.

Primary Examiner—Shep K. Rose
Attorney, Agent, or Firm—Steele, Gould & Fried

[57] ABSTRACT

Fascioliasis vaccine, especially for bovine administration, can be prepared by gamma irradiation of *Fasciola gigantica* metacercariae which can be obtained by infecting *Lymnaea natalensis* snails with *Fasciola gigantica* miracidia and growing the snails until they shed cercariae which encyst to become metacercariae.

3 Claims, No Drawings

PROCESS FOR PRODUCING FASCIOLIASIS VACCINE

The discovery of bovine fascioliasis vaccine results from an intensive study of the biological life cycle of *Fasciola gigantica*, the causative agent of bovine fascioliasis in cattle. The life cycle of this parasite involves the use of *Lymnaea natalensis*, a fresh-water snail, as the immediate host, and mammals, e.g. cattle and sheep, as the definitive hosts. A developmental stage in this parasite's biological life cycle called the metacercarial is formed after the cercariae have become encysted on being shed by the freshwater snail, *Lymnaea natalensis*. The life cycle of *Fasciola gigantica* (the common liver-fluke) is as follows:

The adult fluke normally lives in the bile ducts of its definitive hosts which are usually cattle, sheep, goats etc. In the bile duct, the adult fluke lays large numbers of eggs which pass into the bowel and so escape from the body in the faeces of the host. Each egg hatches and releases a small larva (MIRACIDIUM) within seventeen days under suitable conditions of temperature (26° C.) and moisture. The miracidium swims about in the water and can survive for about 8 hours in search of a freshwater snail known as *Lymnaea natalensis* which it penetrates to continue with further development.

The miracidium usually migrates to the pulmonary chamber of the snail where it becomes a sporocyst. Each sporocyst produces several radiae in the portal system of the snail. The free radiae ultimately produce hundreds of cercariae which swim about in the water and encyst on grass, under-surface of leaves or on some other object. The encysted cercariae (METACERCARIAE) can survive almost for twelve months in the tropics. Once the encysted cercariae are swallowed by the host animal they excyst in the gut to juvenile flukes which penetrate the mucosa of the small intestine, and migrate through the body cavity to the liver. The juvenile flukes penetrate the liver through the liver capsule and move extensively into the parenchyma. After ten weeks of extensive migration and traumatic damage in the liver substance, the flukes settle in the bileducts and start sucking blood from the host and producing eggs again to repeat the cycle in a period of thirteen weeks from the time of swallowing encysted cercariae (METACERCARIAE).

The invention in its broadest sense provides a process for producing a fascioliasis vaccine, particularly for bovine administration, which comprises breeding snails of the species *Lymnaea natalensis*, infecting said snails with *Fasciola gigantica* miracidia, growing the infected snails until they shed *Fasciola gigantica* cercariae, which thereupon encyst to become metacercariae, collecting said metacercariae, subjecting said metacercariae to gamma irradiation from a radioactive source to reduce substantially the pathogenic character of flukes excysting from said metacercariae in the gut of an animal to which metacercariae have been administered relative to flukes so excysting from non-irradiated metacercariae but without substantially altering the immunogenic character of said metacercariae, and collecting said irradiated metacercariae to constitute the effective ingredient of said vaccine. The invention also includes the resulting vaccine.

The expression "substantially reduced pathogenic character" means that the flukes have no pathogenic character or pathogenic character only to such degree that the animal to which the metacercariae is administered contracts fascioliasis in a mild form only. It is naturally preferred that the excysting flukes should possess no pathogenic character.

The radiation dosage to the metacercariae is conveniently in the range from 2500 to 3500 rads, for example in the range from 2800 to 3200 rads. Preferably, the metacercariae are subjected collectively to a uniform radiation dosage of about 3000 rads at a temperature of about 20° C.

Conveniently, the irradiation will be provided by a caesium-137 source. This has a high activity of 10,500 Ci ($\pm$5%) and a half-life of 30 years and is in general used with appropriate shielding by depleted uranium suitably enclosed in a steel case, its longevity of use, energy output and the versatility of the equipment making Cs-137 a superior rdioactive source to Cobalt-60. In practice, irradiation will be provided by a radiation machine having such a source and capable of delivering 200 Krd/h. Such machine should preferably have three sources of radiation.

In a particular embodiment of the invention, the vaccine is in capsule form, the metacercariae having been encapsulated prior to irradiation. Suitably each capsule contains about 1,000 metacercariae and appropriate adjuvants. Once formed, the vaccine should in general be stored at 4° C. or below.

The metacercariae can be produced from *Lymnaea natalensis* on a laboratory scale by culturing the latter in glass or perspex tanks each initially containing about 100 snails, and placed on a bench above ground level. The bottom of each tank is suitably covered with sand obtained from a natural habitat of *L. natalensis*. Conveniently the rest of the tank is three-quarters filled with filtered pond water. Water lilies complete with their root systems from the same habitat are desirably sunk into the tanks, and their roots embedded in the sand, the leaves resting on the water surface. Aeration of the tanks can be obtained from their permanently open tops and by artificially pumping air through the water using a 'Hy-Flo' model 'B' aeration pump. One or two leaves of lightly boiled lettuce are desirably added to each tank once a week to supplement algae, the main food supply for the snails.

In order to achieve large-scale production of the vaccine it is necessary to have large-scale production of the metacercariae and this in turn requires large-scale breeding of the snails. It would of course be possible for collectors to collect an individual snail of this species from its natural habitat, to infect it and to collect the encysted cercariae when they are shed but such an individual procedure is clearly impractical on a large scale.

We have developed a method of manufacturing the metacercariae on a large-scale which is suitable for industrial realisation in the production of fascioliasis vaccine.

According to the present invention an industrial-scale process for the manufacture of *Fasciola gigantica* metacercariae for use in producing fascioliasis vaccine, comprises breeding *Lymnaea natalensis* snails successively in a series of breeder tanks, surviving breeder snails being transferred from one breeder tank to another after their first-generation descendants have been produced and these first-generation descendants being transferred from their respective breeder tank to one or more ancillary cultivation tanks after having been infected with *F. gigantica* miracidia, growing the infected snails in the cultivation tank or tanks until they begin to shed cercariae, which encyst to become metacercariae, and collecting the metacercariae. These metacercariae may then be irradiated as explained above to form the vaccine.

Suitably at least 500, preferably 800–1200, fully-grown breeder snails are introduced into the first breeder tank, these breeder snails suitably being a field strain of the snails collected from their natural habitat, and surviving breeder snails from this tank can be transferred to the next breeder tank (and so on down the line) in 2–4 months, after the first generation of laboratory-bred snails has been produced. In the preferred embodiment these breeder snails are never infected. When all the breeder snails and laboratory-bred snails have been transferred from the first breeder tank this can be re-stocked with a fresh group of wild snails and the cycle recommenced.

The laboratory-bred snails from the breeder tanks are preferably distributed into several individual cultivation tanks as each breeder snail can be expected to produce on average about 100 first-generation descendants in each breeding period. Suitably there are more than 4, preferably 6 to 10, cultivation tanks associated with each breeder tank, although one cultivation tank may, if desired, be associated with more than one breeder tank.

The infection of the laboratory-bred snails, the cultivation of these snails and the collection of the metacercariae may be carried out in any convenient manner.

For the purpose of producing enough dosage of the "Bovine Fascioliasis vaccine" to cater for its African Market, a possible outline of production is as follows:

Each snail is a hermaphrodite individual capable of producing at least 100 eggs per day and a snail egg takes approximately six weeks for the young snail to hatch out and to reach egg-producing stage. A minimum economic unit for industrial-scale production should contain approximately 1,000,000 breeding *L. natalensis* snails, which implies a need for 1,000 tanks.

It is the progeny of these snails that will be suitable for infection with suitable doses of miracidia under appropriate conditions of temperature, pressure and moisture. After an appropriate period of the infection maturation inside the snails, the metacercariae (mc) should be produced at the rate of approximately 10 mc per snail per day, so that the progeny population from the entire stock should be approximately 10,000,000 young snails per day. Assuming 10% of the egg population will survive to continue the generation, the metacercarial production should therefore be 100,000,000 mc per day, i.e. 3,000,000,000 per month. As each dose of the vaccine suitably contains about 1,000 gamma irradiated mc, dose production per month could be 3,000,000.

Further details concerning the performance of the invention in one embodiment are as follows:

EXAMPLE 1

*LYMNAEA NATALENSIS* CULTURE

A laboratory culture of *L. natalensis* is started by collecting a field strain of the snails from Ondiri swamp, Nairobi Dam, Sukari Dams or several other water catchments in and around Nairobi. The seeding of specially prepared aquaria or breeding tanks is done by putting 1000 freshly collected *L. natalensis* from the natural habitat into a first breeder tank. Identification of the snail is confirmed by its characteristic appearance. The shells are dextral and oblong. They are 8–25 mm. high and have 3 or 4 whorls rapidly increasing in size, the ultimate whorl forming almost the entire shell. The columellar margin of the aperture is twisted and the outer lip sharp. The spire is depressed and about half the height of the aperture. The shells are colourless, yellow or dark.

The aquaria systems are set close together but independent of one another as far as the working mechanisms are concerned. An aquarium essentially consists of a glass tank of 60 cm.×30 cm.×30 cm. containing about 30,000 cc, of tap water continuously filtered and maintained at 24° to 27° C. Each tank is kept under fluorescent light for 12 hours during the day time only. The first breeder tank is surrounded by 8 symmetrically arranged cultivation tanks. First generation snails from the first breeder tank are distributed into the surrounding cultivation tanks after infecting them with approximately 5 *Fasciola gigantica* miracidia per snail. Snail infection is done 3 months after initial seeding of the breeder tank. As first generation snails get infected with miracidia and transferred to the surrounding cultivation tanks, the surviving breeder snails are removed from the first breeder tank and transferred to a second breeder tank, similarly surrounded by cultivation tanks, and the process of breeding and infection started all over again. It is reckoned that one unit could contain 5 breeder tanks and associated cultivation tanks of the size mentioned above in a production plant unit measuring 10×5 meters and still leave adequate unoccupied space for carrying out other activities connected with breeding, infection of snails, production of metacercariae and storage of vaccine doses.

Considering the performance of the first breeder tank and its surrounding cultivation tank system we should be able to get a yield of 100,000 infected snails, each shedding 100 metacercariae per month, i.e. a yield of 10,000,000 *F. gigantica* metacercariae or 10,000 doses of the vaccine, from one unit system of tanks. This rate of production can be repeated once a month and with as many doses as possible depending on how many tank units one can set up.

EXAMPLE 2

SNAIL INFECTION WITH *FASCIOLA GIGANTICA* MIRACIDIA

*F. gigantica* eggs are obtained from the bile of affected cattle in the local abattoir. The bile is washed through a 60-mesh sieve (aperture: 250 μm), using tap water, and the eggs collected on a 400-mesh sieve (aperture: 37 μm). The eggs are then washed off the 400-mesh sieve into a 500 ml. beaker with tap water until the beaker is three quarters full. The beaker containing the egg-suspension is maintained at 26° C. The eggs will hatch out miracidia in 15–17 days. After 3 months of culture young *L. natalensis* snails with a shell-height of 3–5 mm. are selected from the aquaria. Each snail is exposed to 5 miracidia suspended in a small volume of water in a watch-glass. The miracidia penetrate the body of the snail for further development.

Breeding and infected snails in their aquaria will be maintained on modified aquarian growth food.

Sixty days after infection, the snails will be shedding hundreds of cercariae which immediately encyst and become metacercariae. These are collected by putting a shedding snail into a single tube of No. 3/1 lined with Cellophane (Trade Mark) paper and three-quarters full of water. The tubes containing shedding snails are put in a tube holder and maintained at an ambient temperature of 22° C. to 27° C. in a room for 48 hours. The cercariae will encyst on the Cellophane usually at water level. The metacercariae produced are now adherent on the Cellophane paper. The Cellophane paper is now removed from the specimen tube and laid of a Petri dish before putting the Petri dish into a refrigerator at 4° C. The snail is transferred into another freshly prepared Cellophane-lined tube for 48 hours. This process of metacercarial collection and storage is repeated until the snail dies.

EXAMPLE 3

EFFECTIVENESS OF VACCINE

Twenty-four male calves at the age of 6 months and free from *Fasciola gigantica* were randomly sub-divided into six groups and subjected to the following treatment: two groups received, on Day 0 and Day 42, two oral doses each of 1000 metacercariae of *Fasciola gigantica* which had been gamma-irradiated at a dosage of 3000 rads. One of these groups was challenged, on Day 140, with 1000 infective non-irradiated metacercariae. Another three groups received 1000 infective metacercariae on Day 0, 42 and 140 respectively, and the remaining group served as untreated control. Autopsies were made on Day 84 or 224, and the livers were checked for recovery of developed parasites and histological alterations. Ten weeks after challenge, three animals of each group were injected with $^{125}$I-albumin and $^{59}$Fe as ferric citrate to determine the effects of the administration of metacercariae on albumin and iron turnover.

In the groups double-vaccinated with irradiated metacercariae, autopsy 84 days after challenge revealed five animals with no worm burden and no liver alterations, whereas two calves had a recovery of 1-2% of the challenge dose and slight bile duct thickening. An average recovery of 27% of the challenge dose was observed in the non-vaccinated groups, 182 and 84 days after challenge. Gross and microscopial lesions were found in the livers of these animals. Albumin turnover and catabolic rate was significantly increased in the non-vaccinated groups as a result of the infective challenge dose. Iron metabolism was only slightly affected in the non-vaccinated groups as a result of the infective challenge dose. This is attributed to the fact that the animals were killed before anaemia had developed.

EXAMPLE 4

FIELD TRIALS ON VACCINE EFFECTIVENESS

A herd of 60 six-month old bulk calves were castrated and set aside from the rest of the main herd on a ranch in Masindi, Uganda. They were randomly divided into six groups of 10 animals in each group as shown in Table 1. All the experimental calves were kept running, grazing and watering under the same husbandry with the rest of the main herd which consisted of 400 calves.

The calves of group I were each double vaccinated with 1000 gamma-irradiated mc. of F.g. at an interval of 4 weeks between the first and the second dose of vaccination. For attenuation of the metacercariae, irradiation of the mc. was done by giving them a total dose of 3000 rads or 3 Kr. The vaccinated calves were each challenged with 1000 non-irradiated metacercariae 4 weeks after administration of the second vaccinating dose. Twelve months after challenge the steers were slaughtered and their livers thoroughly examined for the presence of absence of flukes and lesions.

Blood samples were taken weekly starting one week prior to infection. Faeces samples were taken weekly starting 12 weeks post inoculation.

The calves of groups II, III, IV and V were used as vaccine controls at different levels of vaccination and challenge. Calves of group VI were used as controls of the entire system after artificial challenge of groups I and V calves. The calves of group VI were exposed to natural challenge from the field at the time all the calves of Groups I, IV and V were transferred to the highly endemic paddock and were exposed to drinking water from a stream that run through the paddock. The stream was heavily populated with infected and non-infected *Lymnaea natalensis* snails.

A similar type of field experiment was arranged on a farm at Sumaru, Zaria in Nigeria. Similar environmental conditions did obtain on this farm except that in addition to a stream which run through the challenge paddock, there was a big dam which was full of *Lymnaea natalensis* snails. A herd of 30 calves of the same age vide supra but of mixed sex were obtained and divided randomly into six groups of 5 calves in each group. They were treated like those in Uganda vide supra.

At slaughter of the steers, note was taken of the weight of liver, portal lymph nodes, number and size of the flukes recovered. Fertility of the flukes recovered was also checked for by microscopic examination of individual flukes.

TABLE I

DIAGRAMATIC LAY-OUT OF FIELD CATTLE VACCINATION EXPERIMENTS

| Group | No. of Calves | First Vaccination | Second Vaccination | Challenge | Kill |
|---|---|---|---|---|---|
| IN UGANDA | | | | | |
| I | 10 | V —4 W— V | —4 W— | C —12 MONTHS— | K |
| II | 10 | C —4 W— K | | | |
| III | 10 | | C —4 W— | | K |
| IV | 10 | V — | V | —13 MONTHS— | K |
| V | 10 | | | C —13 MONTHS— | K |
| VI | 10 | | | N —13 MONTHS— | K |
| IN NIGERIA | | | | | |
| I | 5 | V —4 W— V | —4 W— | C —12 MONTHS— | K |
| II | 5 | C —4 W— K | | | |
| III | 5 | | C —4 W— | | K |
| IV | 5 | V —4 W— | V | —13 MONTHS— | K |
| V | 5 | | | C —13 MONTHS— | K |
| VI | 5 | | | N —13 MONTHS— | K |

KEY:
V = Vaccinate the calf with 1000 gamma-irradiated metacercariae of *Fasciola gigantica*
C = Infect the calf with 1000 non-irradiated metacerciae of *Fasciola gigantica*
K = Slaughter or autopsy the calf at the end of experiment
N = Expose the calf to infection naturally in the field
W = Week.

RESULTS

Survival

All the calves of groups I and IV in Uganda and Nigeria survived the entire 14 months of the experiment and were killed at the end of this period. In Uganda and Nigeria, all the calves of groups II and III survived the 4 weeks post-inoculation but were killed at the end of that period. Calves of group V in Uganda died 6 months post-inoculation and exposure to natural infection whereas those in a similar group in Nigeria died 5 months post-inoculation and exposure to natural infection. Group VI steers in Uganda and Nigeria died of natural infection between 10 and 12 months after exposure to natural infection.

Fluke-recovery

The recovery of flukes from all the calves after death in Uganda and Nigeria is to be considered together and it is recorded in the accompanying tables:

| Uganda Cattle Group Mean Parasitological Data Analysis | | | |
|---|---|---|---|
| Group | Wt. of Portal Lymph Nodes | Fluke No. Recovered | % Protection |
| I | 280 g | 5.1 | 99.83 |
| II | 221 g | 601.7 | 39.93 |
| III | 189 g | 660.6 | 33.94 |
| IV | 263 g | 0.7 | 99.97 |
| V | 230 g | 566.0 | 44.0 |
| VI | 211 g | 263.8 | — |

| Nigerian Cattle Group Mean Parasitological Data Analysis | | | |
|---|---|---|---|
| Group | Wt. of Portal Lymph Nodes | Fluke No. Recovered | % Protection |
| I | 267 g | 0 | 100 |
| II | 232 g | 550.4 | 44.96 |
| III | 203 g | 477.6 | 52.24 |
| IV | 270 g | 7 | 99.30 |
| V | 196 g | 534.2 | 46.58 |
| VI | 203 g | 529.8 | — |

Haematological Observations

Blood samples were taken from all the calves throughout the period of the two experiments for the purpose of determining the calves' packed-cell-volumes percentages (PVC) using a Hanksley microhaematocrit centrifuge and reader. Since the layout and performance of the Uganda and Nigeria experiments were the same, it is found necessary to present results of the groups together.

Group I calves in Uganda and Nigeria behaved much in the same way as far as packed-cell-volume percentages are concerned. The mean values of the calves before vaccination were 40%, 4 weeks post vacination they were 38%, and finally the P.C. V. percentages were 40%. Calves of groups II, III and V started with a mean PCV of 35-40% but it declined to 28-32% by 4 weeks post infection when they were autopsied. The calves of group IV had their PCV behaving in the same way as that of Group I throughout the experimental period. Calves of Group VI started with a PCV of 35-37% before they were exposed to the infection. Five months after exposure their P.C.V. was running to between 25% and 20%. Their PVC continued to go down throughout the experimental period and the calves became weaker and weaker until their mean PVC was about 9% at 12 months post exposure and they were autopsied.

Faecal Fasciola Egg Examination

Generally the method of Bitakaramire (1967) was used to determine egg output. No Fasciola eggs were detected in the faeces of groupes I, II, III and IV calves in Uganda and Nigeria. Group V calves in Uganda became patent 14 weeks post infection whereas those in Nigeria became patent 13 weeks after infection. Faciola eggs per gram of faeces continued to be secreted in the faeces of all the calves of the group in Uganda and Nigeria, throughout the period of the experiment. Calves of Group VI became patent 14 weeks post exposure into the infective paddocks. Their mean faecal egg count started at 10 e.p.g. and rose up to approximately 500 e.p.g. over the 12 months of exposure, up to the time they were autopsied.

Pathological Findings

No gross or microscopic lesions were seen in the livers of groups I or IV calves. The only abnormality constantly observed in these calves was gross enlargement of portal lymph nodes.

There was gross enlargement of portal lymph nodes in calves of groups II and III. There were haemorrhages and burrows in and under the liver capsule and in the parenchyma of calves II and III groups. Their liver capsules had been punctured in several places and flukes could be seen crawling on the liver surface.

Portal lymph node gross enlargement in calves of groups V and VI was obvious. Their livers were chronically altered. The bile ducts were seriously enlarged, thickened and fibrosis was observed as if it radiated from their walls, and fibres extended into the parenchyma. Histopathologically several types of liver fibrosis and hyperplastic cholengitis could be seen. The fibrosis could be arranged as follows:

(a) Postnecrotic fibrosis
(b) Ischaemic necrosis and fibrosis
(c) Peribiliary fibrosis
(d) Perilobular fibrosis The first two types of fibrosis appeared to be the effect of migration of young flukes through the parenchyma. Peribiliary fibrosis was linked with the presence of parasites in the bile ducts. Perilobular or monolobular fibrosis described the situation where portal canals, were linked by fibrous tissue. This could have been the result of a phlebitis of the portal vein. The presence of lymphoblasts followed by eosinophilic cells could have been due to the presence of an immuno-mechanism. Another contribution to the possible presence of immuno-mechanism phenomena in the livers of these calves is the increasing population of plasma cells, lymphocytes, macrophages, eosinophilic cells, mast cells and globule leucoeytes in the biliary mucosa.

CONCLUSION

The results obtained from field experiments conducted in Uganda and Nigeria on vaccination of cattle against bovine fascioliasis using gamma-irradiated metacercariae of *Fasciola gigantica* have encouraged us in an effort to try and produce "Bovine Fascioliasis Vaccine". There is every indication that the experiments were successfully conducted and the vaccinated cattle were protected from the disease.

I claim:

1. A process for producing a fascioliasis vaccine which comprises breeding snails of the species *Lymnaea natalensis*, infecting said snails with *Fasciola gigantica* miracidia, growing the infected snails until they shed *Fasciola gigantica* cercariae, which thereupon encyst to become metacercariae, collecting said metacercariae, subjecting said metacercariae to a uniform gamma irradiation dosage of from 2500 to 3500 rads from a radioactive caseium-137 source to destroy the pathogenic character of flukes excysting from said metacercariae in the gut of an animal to which said metacercariae have been administered but without substantially altering the immunogenic character of said metacercariae, and collecting said irradiated metacercariae to constitute the effective ingredient of said vaccine.

2. A process as claimed in claim 1 wherein the metacercriae are encapsulated in an administrable form in a sealed capsule prior to irradiation.

3. A process for producing a fascioliasis vaccine which comprises breeding *Lymnaea natalensis* snails successively in a series of breeder tanks, transferring surviving breeder snails from one breeder tank to another after their first-generation descendants have been produced and these first-generation descendants being transferred from their respective breeder tank to one or more ancillary cultivation tanks after infecting them with *Fasciola gigantica* miracidia, growing the infected snails in the cultivation tank or tanks until they shed *Fasciola gigantica* cercariae, which encyst to become metacercariae, collecting said metacercariae and subjecting them to a uniform gamma irradiation dosage of from 2500 to 3500 rads from a radioactive casium-137 source source to destroy the pathogenic character of flukes excysting from said metacercariae have been administered but without substantially altering the immunogenic character of said metacercariae, and collecting said irradiated metacercariae to constitute the effective ingredient of said vaccine.

* * * * *